United States Patent
Park et al.

(10) Patent No.: US 10,335,781 B2
(45) Date of Patent: Jul. 2, 2019

(54) NANOPIPETTE PROVIDED WITH MEMBRANE CONTAINING SATURATED ION-SENSITIVE MATERIAL, METHOD FOR PREPARING SAME, AND ION MEASURING APPARATUS COMPRISING SAME

(71) Applicant: Konkuk University Industrial Cooperation Corp., Seoul (KR)

(72) Inventors: Bae Ho Park, Seoul (KR); Tomohide Takami, Seoul (KR); Jong Wan Son, Seoul (KR); Eun Ji Kang, Gyeonggi-do (KR)

(73) Assignee: KONKUK UNIVERSITY INDUSTRIAL COOPERATION CORP, Seoul (KR)

( * ) Notice: Subject to any disclaimer, the term of this patent is extended or adjusted under 35 U.S.C. 154(b) by 27 days.

(21) Appl. No.: 15/302,641

(22) PCT Filed: Nov. 10, 2014

(86) PCT No.: PCT/KR2014/010759
§ 371 (c)(1),
(2) Date: Oct. 7, 2016

(87) PCT Pub. No.: WO2015/174593
PCT Pub. Date: Nov. 19, 2015

(65) Prior Publication Data
US 2017/0028396 A1    Feb. 2, 2017

(30) Foreign Application Priority Data

May 16, 2014  (KR) .................. 10-2014-0059191
May 16, 2014  (KR) .................. 10-2014-0059194
May 16, 2014  (KR) .................. 10-2014-0059196

(51) Int. Cl.
*B01L 3/02*     (2006.01)
*G01N 27/40*    (2006.01)
(Continued)

(52) U.S. Cl.
CPC .............. *B01L 3/021* (2013.01); *B82B 1/00* (2013.01); *G01N 27/283* (2013.01);
(Continued)

(58) Field of Classification Search
CPC ......... B01L 3/021; B82B 1/00; G01N 27/283; G01N 27/3335; G01N 27/40
(Continued)

(56) References Cited

U.S. PATENT DOCUMENTS 4,713,165 A * 12/1987 Conover ............... C12Q 1/001
                                                          204/403.05
2010/0072080 A1   3/2010 Karhanek et al.
(Continued)

FOREIGN PATENT DOCUMENTS

FR     2823140      * 10/2002
JP     20003342697    12/2000
(Continued)

OTHER PUBLICATIONS

Takami, T. (2011). "Separate Detection of Sodium and Potassium Ions with Sub-micropipette Probe." Japanese J App Phys. 50. 08LB13. 1-4.*

(Continued)

*Primary Examiner* — Jill A Warden
*Assistant Examiner* — Jacqueline Brazin
(74) *Attorney, Agent, or Firm* — Wenderoth, Lind & Ponack, L.L.P.

(57) ABSTRACT

Disclosed are a nanopipette provided with a membrane containing a saturated ion-sensitive material, a method for
(Continued)

preparing the same, and an ion measuring apparatus comprising the same.

17 Claims, 6 Drawing Sheets

(51) Int. Cl.
  *G01N 27/327* (2006.01)
  *G01N 27/333* (2006.01)
  *B82B 1/00* (2006.01)
  *G01N 27/28* (2006.01)

(52) U.S. Cl.
  CPC ......... *G01N 27/3335* (2013.01); *G01N 27/40* (2013.01); *B01L 2200/10* (2013.01); *B01L 2200/12* (2013.01); *B01L 2300/0645* (2013.01); *B01L 2300/0896* (2013.01); *G01N 27/3278* (2013.01)

(58) Field of Classification Search
  USPC ...................................... 422/82.03
  See application file for complete search history.

(56) References Cited

U.S. PATENT DOCUMENTS

2012/0222958 A1    9/2012   Pourmand et al.
2015/0177189 A1    6/2015   Pourmand et al.

FOREIGN PATENT DOCUMENTS

KR    10-2012-0010386    2/2012
KR    10-2014-0015428    2/2014

OTHER PUBLICATIONS

Takami, T. (2011). "Separate Detection of Sodium and Potassium Ions with Sub-Micropipette Probe." Japanese J. of App Physics. 50:08LB13. 1-4.*
International Search Report dated Feb. 25, 2015 in International (PCT) Application No. PCT/KR2014/010759.
Takami et al., "Separate Detection of Sodium and Potassium Ions with Sub-micropipette Probe", Japanese Journal of Applied Physics, vol. 50, Aug. 22, 2011, pp. 08LB13-1 to 08LB13-4.

* cited by examiner

NANOPIPETTE PROVIDED WITH MEMBRANE CONTAINING SATURATED ION-SENSITIVE MATERIAL, METHOD FOR PREPARING SAME, AND ION MEASURING APPARATUS COMPRISING SAME

BACKGROUND OF THE INVENTION

Field of the Invention

The present invention relates to a nanopipette including a membrane containing a saturated ionophore and, more specifically, to a nanopipette including an ion selective membrane exhibiting ion selectivity by containing a saturated ionophore. The present invention relates to a method for manufacturing a nanopipette including a membrane containing a saturated ionophore and, more specifically, to a method for manufacturing a nanopipette including an ion selective membrane exhibiting ion selectivity by containing a saturated ionophore. The present invention relates to an ion measurement apparatus using a nanopipette including a membrane containing a saturated ionophore and, more specifically, to an ion measurement apparatus including an ion selective membrane, which exhibits ion selectivity by containing a saturated ionophore, inside a nanopipette.

Related Art

Ion selective electrode (ISE) is a kind of membrane electrode having a membrane selectively responding to a particular ion in a solution, and the concentration (activity) of ions can be obtained by measuring the electric potential on an interface between the membrane and the solution. Such an ion selective electrode is equally said a potentiometric ion sensor. The ion selective electrode includes an ion selective membrane. The ion selective membrane is in direct contact with the analyte sample to sense the particular ion, thereby generating a voltage, and thus the ion selective electrode is the most important part in the ion selective electrode.

The ion selective electrode can measure the concentration of a particular ion existing in a sample solution, and thus is used in many fields, such as food chemistry, fermentation processes, environment analysis, or clinical chemistry, for example, hemodialysis, hematoma electrolyte continuous automatic measurement, or extracorporeal blood. Meanwhile, the local ion concentration may be measured using a scanning ion-conductance microscope (SICM) employing a nanopipette which can be controlled at the nano-scaled unit, but since the SICM senses the overall ion current, that is, total ion current, it is not easy to confirm a particular ion distribution.

As for the existing ISE method, although the ions to be detected can be measured, the diameter of a pipette tip portion is very large to the millimeter (mm) unit and the concentration range of the measurable ions is also large, and thus, the ISE method has disadvantages in that the measurement of high concentrations is allowable. However, ion filter electrodes have been recently developed in order to solve the size-related problems and the ion detection even at low concentrations.

The ion filter electrode has a membrane type of plasticized PVC formed inside a pipette, and the diameter of a pipette tip can be reduced to several hundred nanometers. However, the ion filter electrode has disadvantages in that an ionophore existing in the PVC membrane cannot be reused after use, and the concentration of one type of desired ion cannot be measured in an aqueous solution containing three or more types of ions.

SUMMARY OF THE INVENTION

In order to solve the disadvantages of conventional ion filter electrodes, the present inventors had tried to selectively detect at least one type of desired ion by applying an ion selective membrane having a saturated ionophore inside a nanopipette.

In a first aspect, disclosed is an ion-selective nanopipette is provided. The ion-selective nanopette comprises an ion selective membrane containing an ionophore, a polymer matrix, and a plasticizer is provided, wherein the ionophore is saturated.

The ion-selective nanopipette according to a first embodiment may include an selective membrane positioned in the middle (middle membrane collector) in a length direction of the nanopipette.

The ion-selective nanopipette according to a first embodiment may include an selective membrane positioned in a lower conical shank (conical shank membrane collector).

In a second aspect, disclosed is a method for manufacturing the ion-selective nanopipette is provided. The method includes:

(a) injecting a membrane forming solution into a nanopipette to form an ion selective membrane, the membrane forming solution containing an ionophore, a polymer matrix, and a plasticizer; and (b) saturating the ionophore in the ion selective membrane.

The method for manufacturing the ion-selective nanopipette according to a first embodiment may include:

(a) preparing a membrane forming solution containing an ionophore, a polymer matrix, and a plasticizer;

(b) injecting DI water into a nanopipette from above the nanopipette;

(c) injecting the membrane forming solution on the DI water to form an ion selective membrane; and (d) injecting an electrolyte onto the ion selective membrane.

The method for manufacturing an ion-selective nanopipette according to the embodiment may further include (e) injecting a solution, which has the same concentrate as the electrolyte injected in step (d), into a lower tip end portion of the nanopipette.

The ion-selective nanopipette manufactured according to the embodiment may include a membrane positioned in the middle (middle membrane) in a length direction of the nanopipette.

The method for manufacturing an ion-selective nanopipette according to a second embodiment may include:

(a) preparing a membrane forming solution containing an ionophore, a polymer matrix, and a plasticizer;

(b) injecting the membrane forming solution to a tip end portion of a nanopipette to form an ion selective membrane; and (c) injecting an electrolyte into the nanopipette from above the nanopipette.

The method for manufacturing an ion-selective nanopipette according to the embodiment may further include (d) positioning a lower tip portion of the nanopipette in a solution, which has the same concentrate as the electrolyte injected in step (c).

The ion-selective nanopipette manufactured according to the embodiment may include a membrane positioned in the lower conical shank (conical shank membrane) of the nanopipette.

According to a third aspect,

Disclosed is an ion measurement apparatus including: a nanopipette including a membrane containing an ionophore, a polymer matrix, and a plasticizer; an inner electrode in contact with an internal solution; a counter electrode in contact with an external solution; and a measurement circuit connecting the inner electrode and the counter electrode, wherein the ionophore is saturated. The measurement circuit may include: a current-voltage (IV) converter; an amplifier for transmitting a voltage difference of the inner electrode from the counter electrode; and a detector for detecting a signal.

The nanopipette including the membrane containing the saturated ionophore according to the present invention may selectively detect desired ions. The nanopipette including the membrane containing the saturated ionophore according to the present invention may selectively detect a target ion from a sample solution containing a plurality of ions. In addition, the nanopipette including the membrane containing the saturated ionophore according to the present invention may reuse the membrane inside the pipette.

DESCRIPTION OF EXEMPLARY EMBODIMENTS

Figure 1:
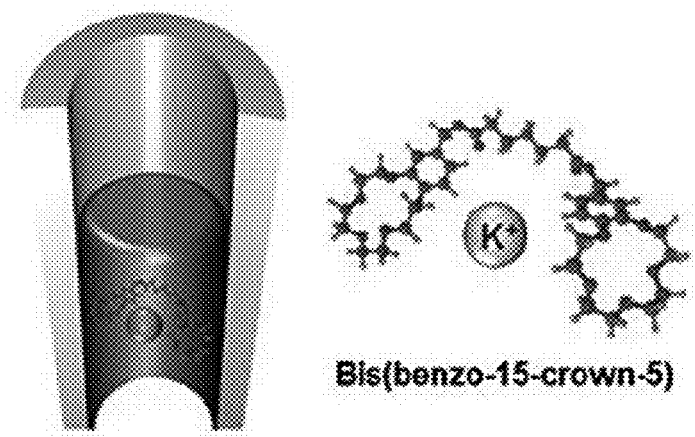
FIG. 1 illustrates one example of a cation-ionophore composite according to the present invention.

Unless defined otherwise, all technical and scientific terminologies used herein have the same meaning as commonly understood by a person having an ordinary skill in the art. Various scientific dictionaries that include the terms included herein are well known and available to those in the art. Although any methods and materials similar or equivalent to those described herein find use in the practice or testing of the present application, some preferred methods and materials are described. It is to be understood that the present invention is not limited to the particular methodology, protocols, and reagents described, as these may vary, depending upon the context in which they are used by those of skill in the art.

As used herein, the singular forms are intended to include the plural forms unless the context clearly indicates otherwise. As used herein, the term "or" means "and/or", unless indicated otherwise. Furthermore, the terms "including" and other forms, for example, "having", "consisting of", and "composed of" are not limited.

The numerical range includes numeric values defined within the range. Every maximum numerical limitation given throughout this specification includes every lower numerical limitation, as if such lower numerical limitations were expressly written herein. Every minimum numerical limitation given throughout this specification includes every higher numerical limitation, as if such higher numerical limitations were expressly written herein. Every numerical range given throughout this specification includes every narrower numerical range that falls within such broader numerical range, as if such narrower numerical ranges were all expressly written herein.

The headings provided herein are not limitations of the various aspects or embodiments of the invention which can be had by reference to the specification as a whole.

According to a first aspect, the present invention provides an ion-selective nanopipette comprising an ion selective membrane (membrane collector) containing an ionophore, a polymer matrix, and a plasticizer, the ionophore being saturated.

As used herein, the term "ion" used herein represents a particular form of an atom or a molecule, and means an atom or a molecule, which has an electric charge due to the lost or gain of electrons. A positively charged ion is called a cation, and a negatively charged ion is called an anion. The ion may be at least one selected from the group consisting of potassium ion ($K^+$), sodium ion ($Na^+$), calcium ion ($Ca^{2+}$), manganese ion ($Mn^{2+}$), copper ion ($Cu^{2+}$), cerium ion ($Ce^{2+}$), and hydrogen ion ($H^+$), but is not limited thereto.

As used herein, the term "nanopipette" refers to a hollow self-supportable, inactive, and non-biological structure having a nano-sized conical tip opening, for example, a tip opening with a diameter of 0.05 nm to 500 nm, 50 nm to 200 nm, or 100 nm to 150 nm. The hollow structure may be formed of, for example, glass or quartz, and may hold a fluid, which passes through the tip opening, therein. The inside of the nanopipette may be selected or transformed so as to minimize the non-specific binding of an analyte. The inside of the nanopipette has an extended conical shape with a uniform wall thickness of a single layer of, generally, quartz or another biological inner material, and may have a size to allow the insertion of an electrode in contact with a solution in the nanopipette. The nanopipette used herein generally has one hole, but a nanopipette having a plurality of concentric holes by withdrawing a double-hole capillary tube. The outer diameter may generally be about 1 μm in a tip region.

As used exchangeably herein, the term "membrane" or "ion selective membrane" refers to a membrane, which is included in an ion selective electrode (ISE) and is in direct contact with an analyte sample to sense a particular ion, thereby generating a current signal through ion exchange, and here, the membrane may be generally composed of an ionophore, a polymer matrix, and a plasticizer.

As used herein, the term "ionophore" refers to a substance which can produce a covalent bond reaction, a coordinate bond reaction, or an ion exchange reaction with the particular ion. The ionophore may be at least one selected from the group consisting of quaternary ammonium salts, valinomycin, valinomycin derivatives, monensin, nonactin, nonactin derivatives, tertiary amines, metal porphyrins, metal phthalocyanines, trifluoroacetophenone, trifluoroacetophenone derivatives, crown ether, dibenzo-18-crown-6, organic phosphor-based ionophores, organic tin-based ionophores, ETH1778, ETH1062, ETH1001, ETH129, ETH149, ETH1644, ETH1117, ETH5214, ETH227, and ETH157, but is not limited thereto.

Figure 2:
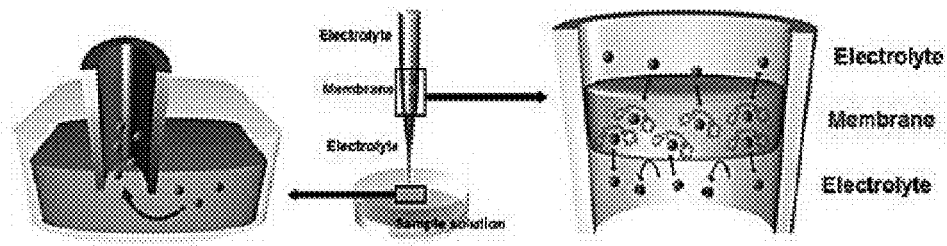
FIG. 2 illustrates a principle of ion exchange of an ion selective membrane positioned in the middle (middle membrane collector) according to the present invention.

FIG. 1 shows an example of the saturated ionophore of the present invention, that is, a cation-ionophore composite; and FIG. 2 shows a principle of ion exchange of an ion selective membrane including the cation-ionophore composite of the present invention.

As used herein, the term "saturated ionophore" means the "cation-ionophore composite" formed by binding an ionophore in the membrane to a cation.

As shown in FIG. 2, the ionophore, which has been previously saturated by a reaction with the ion that is sensed by the ionophore, allows the corresponding ion in the sample through ion exchange to generate a current, thereby enabling the measurement of the selective ion. That is, the ion, such as an ion that is saturated with an ionophore to form a composite, passes through the membrane through ion exchange, but otherwise, the ion is reflected without ion exchange. Therefore, the same ion that saturates an ionophore passes through the membrane by activity through ion exchange to generate a signal, and the application of a different ion does not detect a signal.

Therefore, the nanopipette including a membrane containing the saturate ionophore of the present invention can control the type of ion used to saturate an ionophore, that is, the type of ion sensed by an ionophore.

As used herein, the term "polymer matrix" refers to a structure of a membrane in which different components of a mixture solution constituting the membrane are properly dispersed and maintained to favorably retain characteristics thereof. The polymer matrix may be at least one selected from the group consisting of silicone rubbers, copolymers of poly(bisphenol-A carbonate) and poly(dimethylsiloxane), poly(methylmethacrylate) (PMNIA), polyurethane (PUR or PU), polyetherimide (PEI), and poly(vinyl chloride) (PVC), but is not limited thereto.

As used herein, the term "plasticizer" refers to a non-volatile organic solvent used at a high ratio in order to reduce the rigidity of the polymer matrix. The plasticizer may be at least one selected from the group consisting of o-nitrophenyl octyl ether, bis(2-ethylhexyl)sebacate, dioctyl phthalate, bis(1-butylpentyl)adipate, di octyl phenyl phosphate, tris(2-ethylhexyl)ester, o-nitrophenyl phenyl phosphate, and dibutyl phthalate, but is not limited thereto.

According to the present invention, the ion-selective membrane may further include an anion repeller.

As used herein, the term "anion repeller" reflects an anion, and allows cations to easily approach to around the membrane by reflecting anions. The anion repeller may be at least one selected from the group consisting of triphenyl boron, tris(pentafluoropheneyl)boron), tris(3,5-di(trifluoromethyl)phenyl)boron, tetraphenylborate salt, and tetrakis(pentafluorophenyl)borate salt, but is not limited thereto.

According to a first embodiment of the present invention, the ion-selective nanopipette may include an ion selective membrane positioned in the middle (middle membrane collector) in a length direction of the nanopipette.

Figure 3:
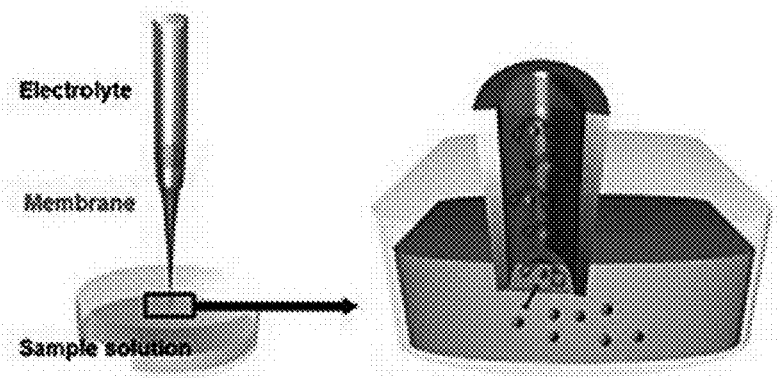
FIG. 3 illustrates a principle of ion exchange of an ion selective membrane positioned in the conical shank (conical shank membrane collector) according to the present invention.

According to a second embodiment of the present invention, the ion-selective nanopipette may include an ion selective membrane positioned in the lower conical shank (conical shank membrane collector) of the nanopipette. FIG. 3 shows a principle of ion exchange of the ion selective membrane positioned in the conical shank.

Specifically, the principle of the ion exchange of the ion selective membrane positioned in the lower conical shank of the nanopipette is the same as that of the ion exchange of the ion selective membrane positioned in the middle in the length direction of the nanopipette. However, the ion selective membrane positioned in the conical shank is formed at the tip portion of the nanopipette to cause ion exchange at the same time when a sample solution is added, and thus the ion selective membrane may generate the activity of ion exchange more promptly compared with the ion exchange in the membrane positioned in the middle in the length direction of the nanopipette, thereby reducing noise and obtaining a more stable signal.

According to a second aspect, the present invention provides a method for manufacturing an ion-selective nanopipette. The method may include the steps of: (a) injecting a membrane forming solution into a nanopipette to form an ion selective membrane, the membrane forming solution containing an ionophore, a polymer matrix, and a plasticizer; and (b) saturating the ionophore in the ion selective membrane.

The membrane forming solution according to the present invention contains an ionophore, a polymer matrix, and a plasticizer, and may further contain an anion repeller. Specifically, the membrane forming solution according to the present invention may be prepared by mixing bis(benzo-15-crown-5) and/or bis(12-crown-4) as an ionophore, PCV as a polymer matrix, o-nitrophenyl octyl ether as a plasticizer, and tetraphenyl borate as an anion repeller at a ratio of 5:32:62:1. The membrane forming solution may be dissolved in tetrahydrofuran. The ionophores, bis(benzo-15-crown-5) and bis(12-crown-4), are represented by chemical formula 1(a) and chemical formula 1(b), respectively:

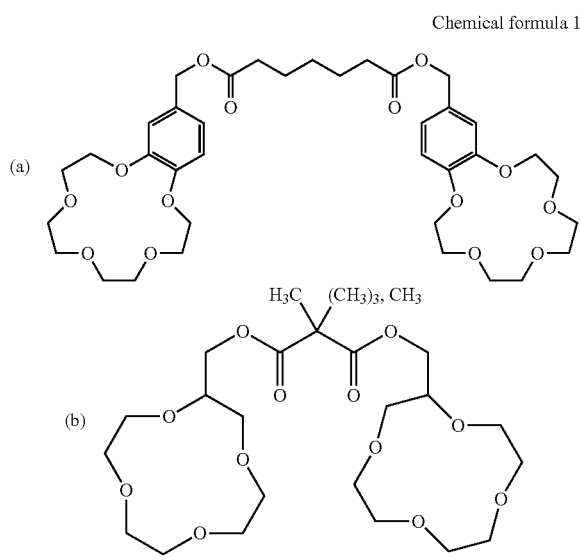

Chemical formula 1

Referring to the above chemical formulas, the rings of bis(benzo-15-crown-5) and bis(12-crown-4) have oxygen bonds, and thus are negatively charged. Therefore, potassium ions and sodium ions may bind to the negatively charged portions. The size of the potassium ions is approximately 152 pm, and the size of the sodium ions is approximately 116 pm, and thus they may bind to bis(benzo-15-crown-5) and bis(12-crown-4) depending on the size thereof.

Figure 4:
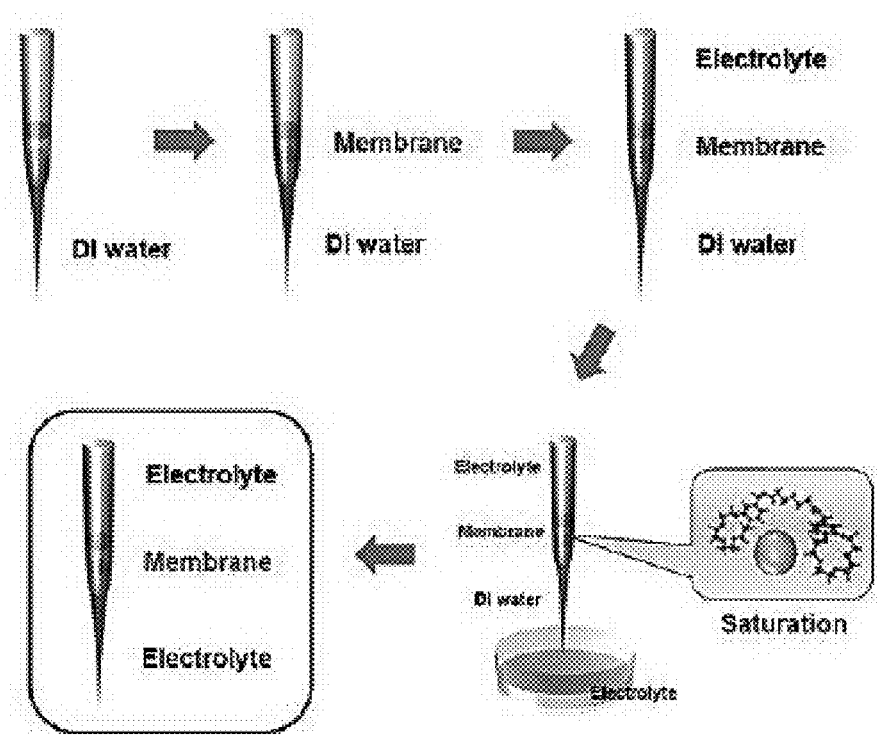
FIG. 4 illustrates a method for manufacturing an ion-selective nanopipette including a membrane positioned in the middle (middle membrane) according to the present invention.

The method for manufacturing the ion-selective nanopipette according to the first embodiment of the present invention may include: (a) preparing a membrane forming solution containing an ionophore, a polymer matrix, and a plasticizer; (b) injecting DI water into a nanopipette from above the nanopipette; (c) injecting the membrane forming solution on the DI water to form an ion selective membrane; and (d) injecting an electrolyte onto the ion selective membrane. The method for manufacturing an ion-selective nanopipette according to the embodiment may further include (e) injecting a solution, which has the same concentrate as the electrolyte injected in step (d), into a lower tip end portion of the nanopipette. The ion-selective nanopipette manufactured according to the embodiment may include a membrane positioned in the middle (middle membrane) in a length direction of the nanopipette. FIG. 4 shows the method for manufacturing an ion-selective nanopipette according to the embodiment.

Referring to FIG. 4, first, DI water is injected to a lower tip portion of a nanopipette from above the nanopipette. A membrane forming solution is injected on the injected DI water, followed by drying, thereby forming an ion selective membrane. In order to saturate an ionophore in the ion selective membrane, an electrolyte is injected into the nanopipette, and then a solution having the same concentration as the electrolyte is injected into a lower tip end portion of the nanopipette, so the ion selective membrane positioned between both of the electrolytes may be saturated. The ions (for example, K+ and/or Na+) existing in the electrolytes bind with the ionophore in the ion selective membrane to form one composite, and thus the ionophore is saturated.

Figure 5:
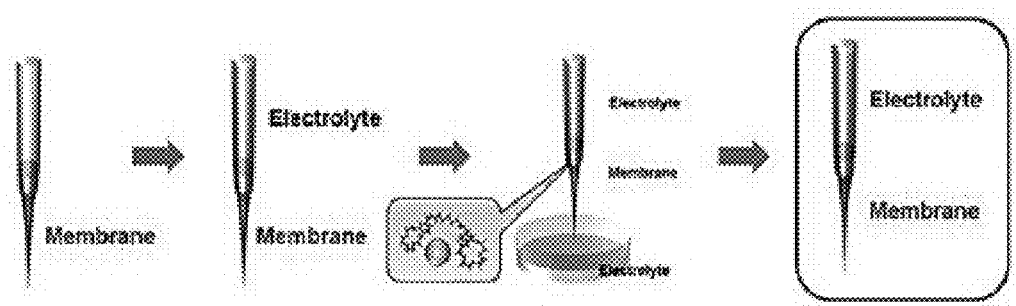
FIG. 5 illustrates a method for manufacturing an ion-selective nanopipette including a membrane positioned in the conical shank (conical shank membrane) according to the present invention.

The method for manufacturing an ion-selective nanopipette according to a second embodiment of the present invention may include: (a) preparing a membrane forming solution containing an ionophore, a polymer matrix, and a plasticizer; (b) injecting the membrane forming solution to a tip end portion of a nanopipette to form an ion selective membrane; and (c) injecting an electrolyte into the nanopipette from above the nanopipette. The method for manufacturing an ion-selective nanopipette according to the embodiment may further include (d) positioning a lower tip portion of the nanopipette in a solution, which has the same concentrate as the electrolyte injected in step (c). The ion-selective nanopipette manufactured according to the embodiment may include a membrane positioned in the lower conical shank (conical shank membrane) of the nanopipette. FIG. 5 shows the method for manufacturing an ion-selective nanopipette according to the embodiment.

Referring to FIG. 5, first, a membrane forming solution is injected into a nanopipette, followed by drying, thereby forming an ion selective membrane. In order to saturate an ionophore in the ion selective membrane, an electrolyte is injected into the nanopipette from above the nanopipette, and then a lower tip portion of the nanopipette is positioned in a solution having the same concentration as the electrolyte, so the ion selective membrane positioned between both of the electrolytes may be saturated. The ions (for example, K+ and/or Na+) existing in the electrolytes bind with the ionophore in the ion selective membrane to form one composite, and thus the ion selective membrane is saturated.

Figure 6:
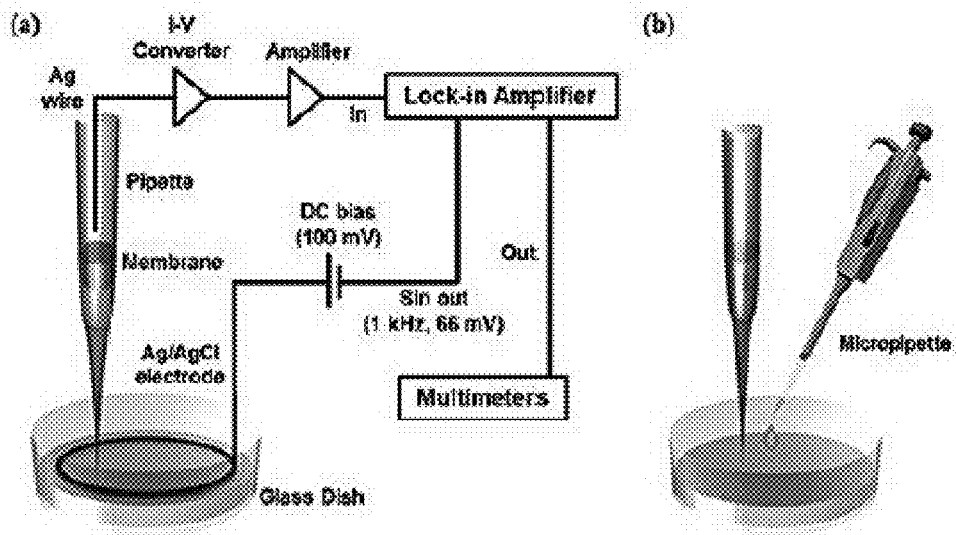
FIG. 6 illustrates one example of an ion selective electrode according to the present invention.

According to a third aspect, the present invention provides an ion measurement apparatus including: a nanopipette including a membrane containing an ionophore, a polymer matrix, and a plasticizer; an inner electrode in contact with an internal solution; a counter electrode in contact with an external solution; and a measurement circuit connecting the inner electrode and the counter electrode, wherein the ionophore is saturated. The measurement circuit may include: a current-voltage (IV) converter; an amplifier for transmitting a voltage difference of the inner electrode from the counter electrode; and a detector for detecting a signal. FIG. 6 shows an example of the ion measurement apparatus according to the present invention.

As used herein, the term "internal solution" refers to a solution containing an electrolyte for obtaining an ion current signal. The electrolyte is a material containing free ions, and may be at least one selected from the group consisting of sodium, potassium, calcium, magnesium, chloride, phosphate, and bicarbonate, but is not limited thereto.

As used herein, the term "external solution" refers to a sample solution containing an ion to be measured, and may contain living cells, plasma, and other body fluids.

As used herein, the term "measurement circuit" measures a particular ion signal by alternating current (AC), and the output current follows the change in the input voltage, and thus even a small change in the current may be detected.

The nanopipette including the membrane containing the saturated ionophore according to the present invention may selectively detect desired ions according to the kind of ionophore, and the kind of ion saturating the ionophore. The nanopipette including the membrane containing the saturated ionophore according to the present invention may selectively detect a target ion from a sample solution containing a plurality of ions. In addition, the nanopipette including the membrane containing the saturated ionophore according to the present invention may reuse the membrane inside the pipette.

Hereinafter, various examples will be set forth for better understanding of the present invention. The following examples are merely for illustrating the present invention, and thus are not intended to limit the scope of the present invention.

EXAMPLES

Example 1: Manufacturing of Nanopipette

A nanopipette with a diameter of 100 nm was manufactured from a borosilicate glass capillary tube with a filament (GD-1, Narishige) by using a $CO_2$-based puller (Model P-2000, Sutter Instrument). Here, the used puller was set as follows:

Heat=350, Filament=3, Velocity=30, Delay=190, Pull=0; and

Heat=330, Filament=2, Velocity=27, Delay=180, Pull=250.

Figure 7:
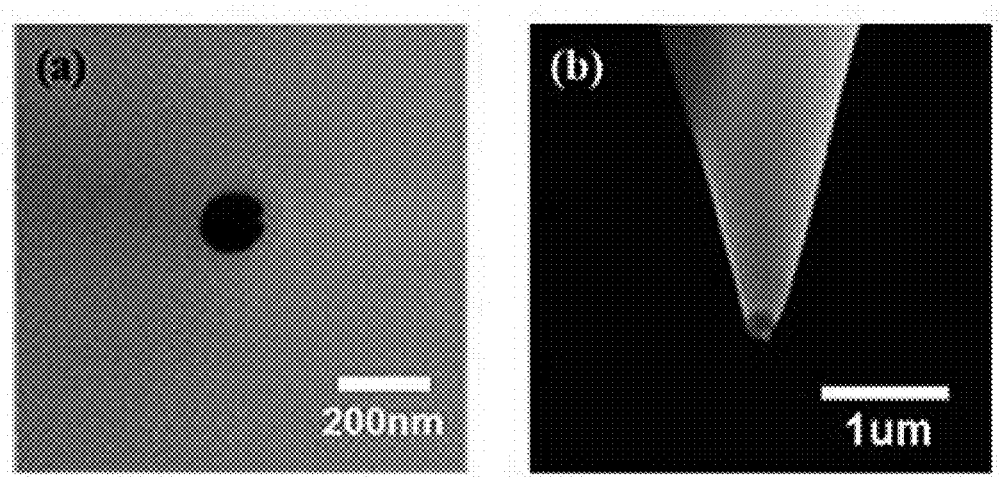
FIG. 7 shows SEM measurement results of a nanopipette manufactured according to the present invention.

The manufactured nanopipette was observed through scanning electron microscope (SEM), and the results are shown in FIG. 7.

Example 2: Preparation of Membrane Forming Solution

A membrane forming solution, which contains an ionophore (bis(12-crown-4) (Dojindo CAS 80403-59-4)), PVC (Aldrich, CAS 9002-86-2), a plasticizer ((o-nitrophenyloctylether (Aldrich, CAS 3244-41-5)), and an anion repeller (tetraphenyl borate) at a weight ratio of 5:32:62:1, was prepared. In addition, a membrane forming solution was prepared by the same method except that bis(benzo-15-crown-5) (Dojindo CAS 69271-98-3) was used as an ionophore.

Example 3: Manufacturing of Ion Selective Electrode (Ion Collector Electrode)

(1) Preparation of Ion Selective Membrane Positioned in Middle (Middle Membrane Collector)

Two nanopipettes manufactured in example 1 were prepared, and, for each of the nanopipettes, DI water was injected to a lower tip end portion of the nanopipette from above the nanopipette using a thin injection needle. Then, the membrane forming solutions prepared in example 2 were put on the DI water, which has been injected into the nanopipettes, respectively, followed by drying in a dry box for 2 hours, thereby forming membranes. $4 \times 0^{-3}$ M potassium chloride (KCl) and sodium chloride (NaCl) solutions were injected on the membranes, respectively, and the same solutions were injected into the lower tip end portions of the nanopipettes, respectively. Then, the resultant nanopipettes were stored in a dry box for two days, thereby completing a potassium selective membrane saturated with potassium ions and a sodium selective membrane saturated with sodium ions, respectively.

(2) Preparation of Ion Selective Membrane Positioned in Conical Shank (Conical Shank Membrane Collector)

Two nanopipette manufactured in example 1 were prepared, and the membrane forming solutions prepared in example 2 were injected to the tip portions of the nanopipettes, followed by drying in a dry box for two hours, thereby forming membranes. Here, the tip portions of the nanopipettes were soaked in DI water, thereby preventing the hardening of the membrane forming solutions. Then, $4 \times 10^{-3}$ M potassium chloride (KCl) and sodium chloride (NaCl) solution was injected, from above the nanopipettes in which the membranes were formed, into the nanopipettes, respectively, and the tip portions of the nanopipettes were soaked in solutions having the same concentration. Then, the resultant pipettes were stored in a dry box for two days, thereby completing a potassium selective membrane saturated with potassium ions and a sodium selective membrane saturated with sodium ions.

Figure 8:
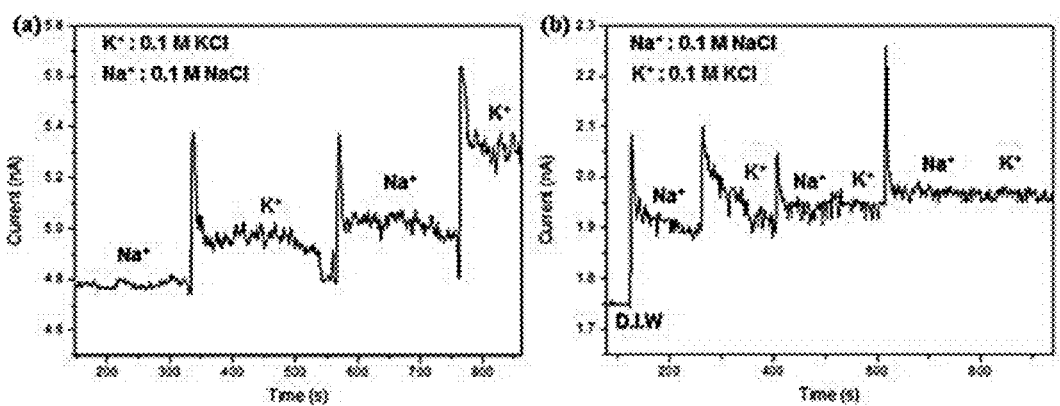
FIG. 8 shows ion selective measurement results of an ion membrane positioned in the middle region according to test example 1 of the present invention.

Test Example 1: Measurement Results of Ion Selectivity of Nanopipette Including Membrane Containing Saturated Ionophore According to Present Invention (1) Measurement of Ion Selectivity of Ion Membrane Positioned in Middle The signals of potassium and sodium ions of the potassium selective membrane saturated with potassium ions and the sodium selective membrane saturated with sodium ions, which were prepared in example 3(1), were measured by using a low-current ion signal detection system shown in FIG. 6 (a) and injecting an external solution by the method shown in FIG. 6(b). The results are shown in FIG. 8. FIGS. 8(a) and 8(b) are graphs showing the measurements of potassium and sodium ions, respectively.

As can be seen from FIG. 8(a), the signal was increased when 0.1 M KCl as an external solution was added to the potassium selective membrane, and the height change of the signal was little when 0.1 M NaCl was added. As can be seen from FIG. 8(b), the signal was increased when 0.1 M NaCl as an external solution was added to the sodium selective membrane, and the height change of the signal was little when 0.1 M KCl was added. The signal-to-noise ratios (S/N) of the potassium selective membrane and the sodium selective membrane were 1.75 and 1.06, respectively.

(2) Measurement of Ion Selectivity of Membrane Positioned in Conical Shank

Figure 9:
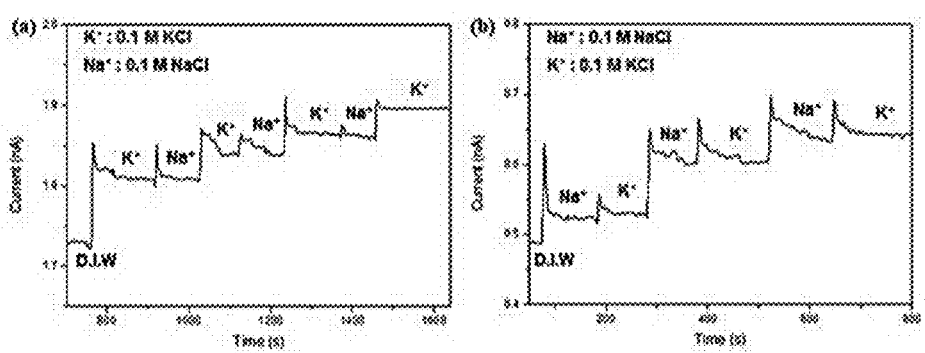
FIG. 9 shows measurement results of ion selectivity of an ion membrane positioned in the conical shank according to test example 1 of the present invention.

The signals of potassium and sodium signals of the potassium selective membrane saturated with potassium ions and the sodium selective membrane saturated with sodium ions, which were manufactured in example 3(2), were measured by the same method as in test example 1(1), and the results are shown in FIG. 9. FIGS. 9(a) and 9(b) are graphs showing the measurements of potassium and sodium ions, respectively.

As can be seen from FIG. 9(a), the signal was increased when 0.1 M KCl as an external solution was added to the potassium selective membrane, and the change of the signal was little when 0.1 M NaCl was added. As can be seen from FIG. 9(b), the signal was increased when 0.1 M NaCl as an external solution was added to the sodium selective membrane, and the change of the signal was little when 0.1 M KCl was added. The signal-to-noise ratios (S/N) of the potassium selective membrane and the sodium selective membrane were 21.68 and 16.57, respectively.

It can be seen from the above results that the S/N ratios of the ion selective membranes positioned in the conical shank were increased by about 15-fold or more compared with the S/N ratios of the ion selective membranes positioned in the middle. In the case of the ion selective membrane positioned in the middle, the electrolyte exists in the tip portion of the nanopipette. Thus, it is verified that, before the ions in the external solution reach the membrane, the noise occurs by the electrolyte existing in the tip portion of the nanopipette.

Test Example 2: Verification of Reproducibility of Conical Shank Membrane

Figure 10:
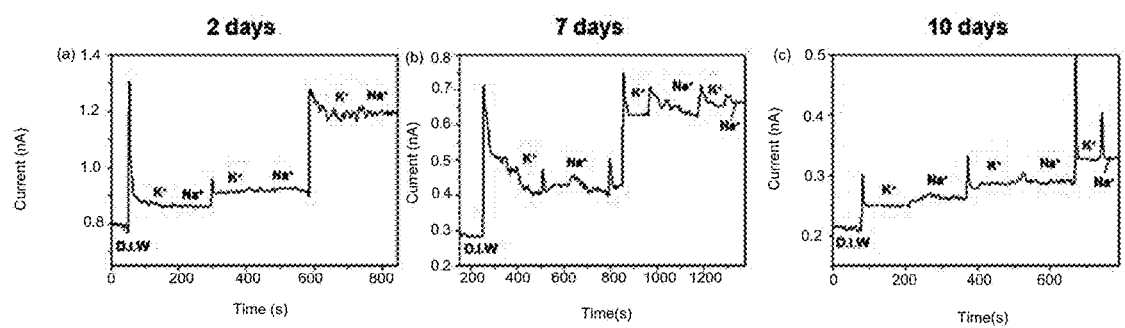
FIG. 10 shows confirmation results of reproducibility of a potassium selective membrane positioned in the conical shank according to test example 2 of the present invention.
Figure 11:
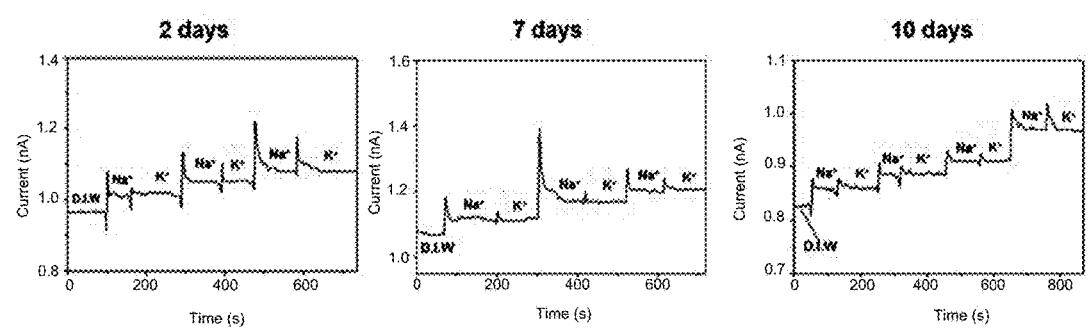
FIG. 11 shows confirmation results of reproducibility of a sodium selective membrane positioned in the conical shank according to test example 2 of the present invention.

The saturation procedures of the ionophores in the potassium selective membrane and the ion selective membrane, which were prepared in example 3(2), were measured for 2, 7, and 10 days by the same method as in test example 1, and the results are shown in FIGS. 10 and 11.

As can be seen from FIGS. 10 and 11, it was verified that, in the case of the conical shank membranes, target ions could be selectively detected even after 2, 7, and 10 days.

As described above, the present invention has been described with reference to preferable embodiments. Those skilled in the art will appreciate that various modifications, additions, and substitutions are possible, without departing from the scope and spirit of the invention as disclosed in the accompanying claims. The disclosed embodiments are accordingly to be considered in an illustrative and not in a limited sense. The scope of the present invention is not defined by the detailed description as set forth above but by the accompanying claims of the invention, and it should also be understood that all changes or modifications derived from the definitions and scopes of the claims and their equivalents fall within the scope of the invention.

INDUSTRIAL APPLICABILITY

The nanopipette including a membrane containing a saturated ionophore according to the present invention can selectively detect a desired ion. The nanopipette including the membrane containing a saturated ionophore according to the present invention may selectively measure a target ion from a sample solution containing a plurality of ions. Furthermore, the nanopipette including the membrane containing the saturated ionophore according to the present invention may be reused.

What is claimed is:

1. An ion-selective nanopipette comprising an ion selective membrane,
    wherein the ion selective membrane comprises a saturated ionophore, a polymer matrix, a plasticizer, and an anion repeller,
    wherein the ion selective membrane is positioned in a lower conical shank (conical shank membrane collector) of the nanopipette, and
    wherein the ion-selective nanopipette generates a current signal by ion exchange with an ion in a sample that is the same ion as that which saturates the ionophore, thereby enabling measurement of the selective ion.

2. The ion-selective nanopipette of claim 1, wherein the ionophore is at least one selected from the group consisting of quaternary ammonium salts, valinomycin, valinomycin derivatives, monensin, nonactin, nonactin derivatives, tertiary amines, metal porphyrins, metal phthalocyanines, trifluoroacetophenone, trifluoroacetophenone derivatives, crown ether, dibenzo-18-crown-6, organic phosphor-based ionophores, organic tin-based ionophores, ETH1778, ETH1062, ETH1001, ETH129, ETH149, ETH1644, ETH1117, ETH5214, ETH227, and ETH157.

3. The ion-selective nanopipette of claim 1, wherein the polymer matrix is at least one selected from the group consisting of silicone rubbers, copolymers of poly(bisphenol-A carbonate) and poly(dimethylsiloxane), poly(methylmethacrylate) (PMMA), polyurethane (PUR or PU), polyetherimide (PEI), and poly(vinyl chloride) (PVC).

4. The ion-selective nanopipette of claim 1, wherein the plasticizer is at least one selected from the group consisting of o-nitrophenyl octyl ether, bis(2-ethylhexyl)sebacate, dioctyl phthalate, bis(1-butylpentyl)adipate, dioctyl phenyl phosphate, tris(2-ethylhexyl)ester, o-nitrophenyl phenyl phosphate, and dibutyl phthalate.

5. The ion-selective nanopipette of claim 1, wherein the anion repeller is at least one selected from the group consisting of triphenyl boron, tris(pentafluoropheneyl)boron), tris(3,5-di(trifluoromethyl)phenyl)boron, tetraphenylborate salt, and tetrakis(pentafluorophenyl)borate salt.

6. The ion-selective nanopipette of claim 1, wherein the ion is at least one selected from the group consisting of potassium ion ($K^+$), sodium ion ($Na^+$), calcium ion ($Ca^{2+}$), manganese ion ($Mn^{2+}$), copper ion ($Cu^{2+}$), cerium ion ($Ce^{2+}$), and hydrogen ion ($H^+$).

7. The ion-selective nanopipette of claim 1, wherein the ion selective membrane is reusable.

8. A method for manufacturing the ion-selective nanopipette of claim 1, the method comprising: (a) injecting a membrane forming solution into a nanopipette to form an ion selective membrane, the membrane forming solution containing an ionophore, a polymer matrix, and a plasticizer; and (b) saturating the ionophore in the ion selective membrane.

9. The method of claim 8, wherein step (a) comprises injecting DI water into the nanopipette from above the nanopipette, and injecting the membrane forming solution on the DI water.

10. The method of claim 9, wherein step (b) comprises injecting an electrolyte, from above the nanopipette in which the ion selective membrane is formed in step (a), into the nanopipette.

11. The method of claim 10, further comprising, after step (b), injecting a solution, which has the same concentration as the injected electrolyte, into a lower tip end portion of the nanopipette.

12. The method of claim 8, wherein step (a) comprises injecting the membrane forming solution to a tip end portion of the nanopipette from above of the nanopipette.

13. The method of claim 12, wherein step (b) comprises injecting an electrolyte, from above the nanopipette in which the ion selective membrane is formed in step (a), into the nanopipette.

14. The method of claim 13, further comprising, after step (b), positioning a lower tip end portion of the nanopipette in a solution having the same concentration as the injected electrolyte.

15. An ion measurement apparatus comprising: the ion-selective nanopipette of claim 1; an inner electrode in contact with an internal solution; a counter electrode in contact with an external solution; and a measurement circuit connecting the inner electrode and the counter electrode.

16. The ion measurement apparatus of claim 15, wherein the measurement circuit comprises: a current-voltage (IV) converter, an amplifier for transmitting a voltage difference of the inner electrode from the counter electrode, and a detector for detecting a signal.

17. The apparatus of claim 15, wherein the external solution corresponds to living cells or plasma.

* * * * *